US010501356B2

(12) United States Patent
Macey

(10) Patent No.: US 10,501,356 B2
(45) Date of Patent: *Dec. 10, 2019

(54) HOSPITAL OZONE FAUCET

(71) Applicant: Franke Technology and Trademark Ltd, Hergiswil (CH)

(72) Inventor: Cory Macey, Midland (CA)

(73) Assignee: Franke Technology and Trademark Ltd, Hergiswil (CH)

( * ) Notice: Subject to any disclaimer, the term of this patent is extended or adjusted under 35 U.S.C. 154(b) by 143 days.

This patent is subject to a terminal disclaimer.

(21) Appl. No.: 15/790,550

(22) Filed: Oct. 23, 2017

(65) Prior Publication Data

US 2018/0141844 A1 May 24, 2018

Related U.S. Application Data

(60) Provisional application No. 62/424,768, filed on Nov. 21, 2016.

(51) Int. Cl.
*A61L 2/03* (2006.01)
*A61L 2/24* (2006.01)
(Continued)

(52) U.S. Cl.
CPC ............ *C02F 9/005* (2013.01); *A61L 2/035* (2013.01); *A61L 2/24* (2013.01); *C02F 1/008* (2013.01);
(Continued)

(58) Field of Classification Search
CPC .. A61L 2/035; A61L 2/24; C02F 1/008; C02F 1/4618; C02F 1/5672; C02F 1/78;
(Continued)

(56) References Cited

U.S. PATENT DOCUMENTS 1,676,035 A * 7/1928 Lehnert .................. B05B 1/04
239/590
3,850,808 A * 11/1974 Hoermann ............ B01D 21/02
210/195.3
(Continued)

FOREIGN PATENT DOCUMENTS

CA 2437426 2/2005
DE 20021035 4/2002
(Continued)

OTHER PUBLICATIONS

Improve Effectiveness of Hand Hygiene Results, Franke, three pages, admitted prior art. (Jan. 1, 2016).

*Primary Examiner* — Lucas A Stelling
(74) *Attorney, Agent, or Firm* — Volpe and Koenig, P.C.

(57) ABSTRACT

A hospital faucet assembly is provided that includes an outlet adapted to direct a flow water stream into a sink. An ozone chamber is provided having a water inlet and a water outlet. A flow control valve is connected to the water inlet, and the water outlet is connected to the faucet armature. A sensor is provided which is adapted to control the flow control valve. An ozone generator is located within the chamber, and when a user activates the sensor, the valve opens allowing more water to enter the chamber and then travel out through the water outlet of the ozone chamber to the faucet armature which dispenses the water flow into the sink. A controller is provided and is connected to the control valve and the sensor. The controller is configured to run an automatic cycle on an occasional basis to flush the sink with ozone-rich water in order flush and/or disinfect water located in a trap of the sink drain, or provide other disinfecting functions.

19 Claims, 3 Drawing Sheets

(51) Int. Cl.
*C02F 1/461* (2006.01)
*C02F 1/467* (2006.01)
*C02F 1/78* (2006.01)
*C25B 1/13* (2006.01)
*E03C 1/046* (2006.01)
*E03C 1/05* (2006.01)
*E03C 1/126* (2006.01)
*C02F 9/00* (2006.01)
*C02F 1/00* (2006.01)

(52) U.S. Cl.
CPC .......... *C02F 1/4618* (2013.01); *C02F 1/4672* (2013.01); *C02F 1/78* (2013.01); *C25B 1/13* (2013.01); *E03C 1/046* (2013.01); *E03C 1/057* (2013.01); *E03C 1/126* (2013.01); *C02F 2001/46185* (2013.01); *C02F 2209/40* (2013.01); *C02F 2209/44* (2013.01); *C02F 2307/06* (2013.01)

(58) Field of Classification Search
CPC ............ C02F 9/005; C02F 2001/46185; C02F 2209/40; C02F 2209/44; C02F 2307/06; E03C 1/046; E03C 1/057; E03C 1/126
See application file for complete search history.

(56) References Cited

U.S. PATENT DOCUMENTS

| | | | |
|---|---|---|---|
| 3,851,825 A * | 12/1974 | Parkison | E03C 1/084 239/590.3 |
| 6,484,953 B2 * | 11/2002 | Freier | E03C 1/08 239/461 |
| 8,319,654 B2 | 11/2012 | Field et al. | |
| 8,440,080 B2 | 5/2013 | Salama et al. | |
| 9,009,882 B2 * | 4/2015 | Bucher | A47K 1/04 4/619 |
| 2002/0146357 A1 | 10/2002 | Yeh | |
| 2004/0083546 A1 * | 5/2004 | Tahara | A47K 1/04 4/619 |
| 2010/0006450 A1 | 1/2010 | Whitehead et al. | |
| 2010/0032312 A1 | 2/2010 | Scarsbrook | |
| 2010/0206409 A1 * | 8/2010 | Gautschi | E03C 1/0404 137/614 |
| 2011/0079519 A1 * | 4/2011 | Widler | C02F 1/4672 205/743 |
| 2012/0124737 A1 | 5/2012 | Gibson | |
| 2012/0138478 A1 | 6/2012 | Yost, III et al. | |
| 2013/0193079 A1 | 8/2013 | Booth et al. | |
| 2013/0206604 A1 | 8/2013 | Lutz et al. | |
| 2013/0206654 A1 | 8/2013 | Lutz et al. | |
| 2014/0352799 A1 * | 12/2014 | Rosko | C02F 1/78 137/237 |

FOREIGN PATENT DOCUMENTS

| | | |
|---|---|---|
| WO | 9802075 | 1/1998 |
| WO | 2007009295 | 1/2007 |
| WO | 2012087302 | 6/2012 |
| WO | 2013086217 | 6/2013 |
| WO | 2016188929 | 12/2016 |

* cited by examiner

HOSPITAL OZONE FAUCET

INCORPORATION BY REFERENCE

The following documents are incorporated herein by reference as if fully set forth: U.S. Provisional Patent Application No. 62/424,768, filed Nov. 21, 2016

FIELD OF INVENTION

The invention relates to a faucet assembly and more particularly to a faucet with an in-line ozone generator.

BACKGROUND

Faucet assemblies that can be used with various sinks and provide for touch-free washing are known. These typically include a proximity sensor on the faucet or in an area of the sink to detect when a user is present, which turns the water on either for a predetermined period or until when the sensor no longer detects the user. In hospitals and other medical or laboratory environments, these are used by various personnel for enhanced cleanliness, which can be critical to prevent the spread of bacteria or other hazardous material. While these are referred to as hospital faucet assemblies, they are often used in other healthcare facilities, laboratories, and other applications, so the designation of "hospital faucet" is considered generic to this type of faucet, regardless of the particular application.

It would be desirable to provide an improved hospital faucet assembly that provides for a disinfecting flow of water in hands-free operation and also provides for further disinfecting operations.

SUMMARY

Briefly stated, a hospital faucet assembly is provided that is retro-fittable to existing sinks. The faucet is connectable to a faucet deck of a sink or an adjacent counter top, and includes an outlet adapted to direct a flow water stream, preferably a laminar flow, into the sink bowl. An ozone chamber having a top and a bottom is provided, and includes a water inlet and a water outlet. A flow control valve is connected to the water inlet, and the water outlet is connected to the faucet. A sensor is provided, preferably on the faucet armature, which is adapted to control the flow control valve. An ozone generator is located within the chamber, which in use is filled with water, and when a user activates the sensor, the valve opens allowing more water to enter the chamber which then travels out through the water outlet of the ozone chamber to the faucet which dispenses the water flow into the sink. The ozone generator located within the chamber allows for various disinfecting functions.

A controller is provided and is connected to the control valve and the sensor. The controller is configured to run an automatic cycle on an occasional basis in which the ozone generator is activated, and after a pre-determined time period, the controller opens the flow control valve to flush the sink with ozone and mixed oxidant-rich water in order flush and/or disinfect water located in a trap of the sink drain.

The controller may be further configured to activate the ozone generator when the sensor is activated by a user to wash a user's hands and the controller opens the control valve. This provides ozone and mixed oxidant supplemented water for washing.

In a further mode, the controller can be configured with an optional disinfecting hand wash mode, in which when a user places their hands in front of the sensor, the valve opens and power is sent to the ozone generator, and when a user moves their hands away from the sensor in order to lather, for preferably a minimum of 20 seconds as recommended by the World Health Organization (WHO), the flow control valve is turned off for a predetermined time period, but the ozone generator continues to run building the ozone and mixed oxidant concentration in the water within the chamber which dramatically improves the effectiveness of continued hand washing during the rinse.

The controller can be further configured to detect a current draw of the ozone generator and adjust the pre-determined time period that the ozone generator is activated to control a concentration of ozone and mixed oxidants in the water in the chamber. The current draw by the ozone generator is dependent on the total dissolved solids (TDS) in the water, with a higher TDS indicating that more ozone and mixed oxidants can be generated per unit time. Accordingly, higher concentrations of ozone and mixed oxidants can be achieved in a shorter time period. In view of this, the time that the ozone generator is on while further water flow is stopped in order to achieve a desired ozone and mixed oxidant level can be shortened.

The controller can be further configured to reverse a polarity of a cathode and an anode of the ozone generator on an occasional basis. This is used to prevent a build-up of minerals and/or metals that are part of the TDS on the cathode. By periodically reversing the polarity of the anode and the cathode, this build-up is limited or reversed, providing a longer life and less maintenance requirements for the system.

Preferably, the ozone chamber is cylindrical and is mountable with an axis of the chamber being vertical. Preferably, the ozone chamber has a capacity of about 0.5 liters to 0.75 liters. The ozone generator preferably extends along the axis of the chamber.

Preferably, the sensor is an IR sensor.

In a preferred arrangement, a nozzle is located in an outlet of the faucet, which is preferably a laminar flow nozzle. The nozzle opening sets the flow rate, which is preferably 1.5-2.2 gallons per minute. However, other flow rates could be provided.

In one particularly preferred arrangement, the controller is further configured to activate in a hand wash mode, in which the sensor detects a user and opens the flow control valve and, when a user moves their hands away from the sensor after an initial delivery of water, the controller is adapted to turn off the flow control valve for a predetermined time period and continues to allow the ozone generator to operate such that a first ozone concentration is reached in the water within the chamber, and then is adapted to turn on the control valve. This allows a user to benefit from an ozone-rich water flow for rinsing their hands. Further, in the disinfection cycle, the ozone generator is activated until the water in the ozone chamber has reached a second ozone concentration, and this second ozone concentration is higher than the first ozone concentration.

In other aspects of the invention, the faucet as well as a method of using the faucet assembly are provided which, along with other aspects and details of the invention, are described below and in the Claims and have not been repeated here and are incorporated by way of reference.

BRIEF DESCRIPTION OF THE DRAWINGS

The foregoing Summary and the following detailed description will be better understood when read in conjunc

DETAILED DESCRIPTION OF THE PREFERRED EMBODIMENTS

Figure 1:
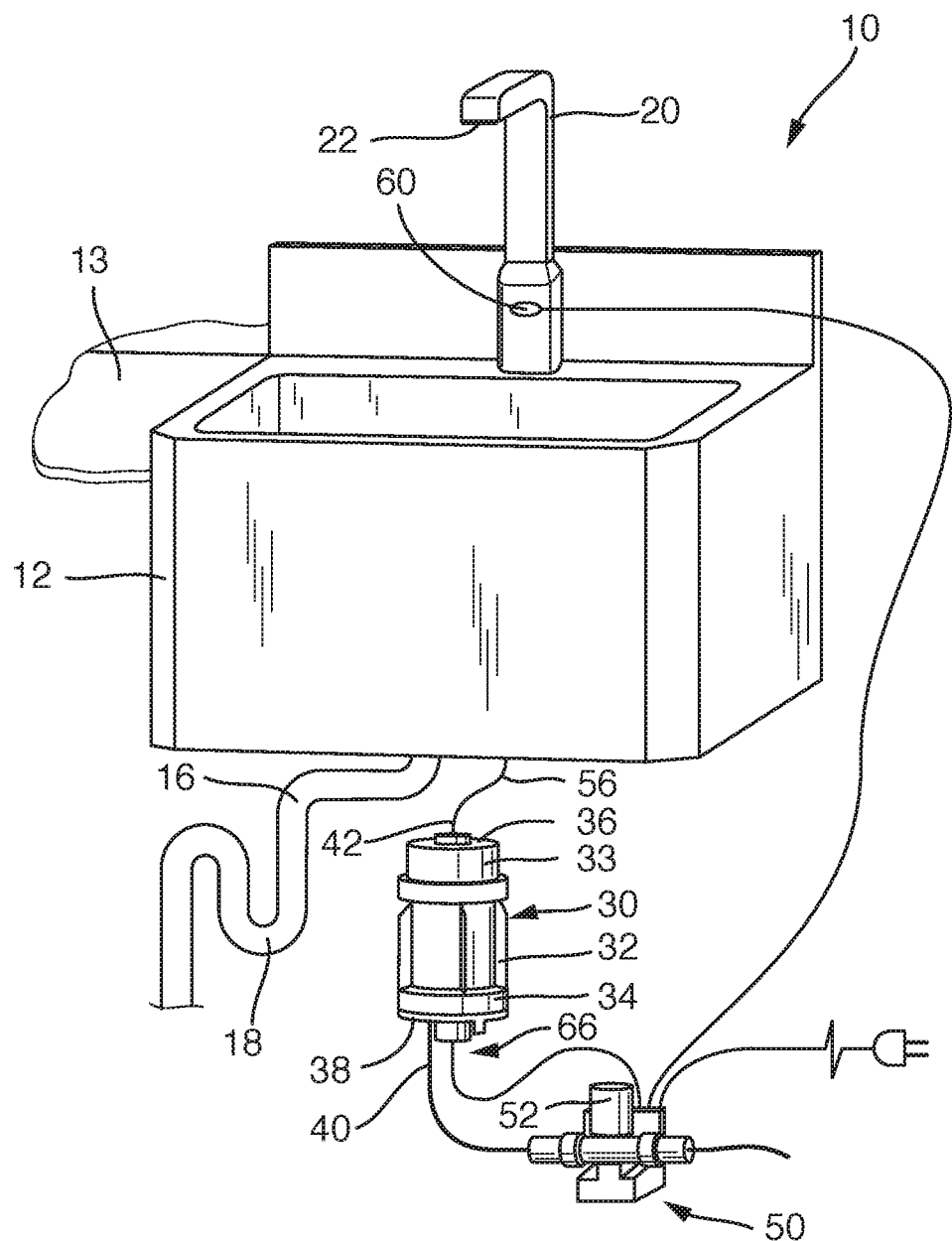
- FIG. 1 is a top, front, right perspective view of a faucet assembly in accordance with one embodiment installed on a sink.

Certain terminology is used in the following description for convenience only and is not limiting. The words "front," "rear," "upper" and "lower" designate directions in the drawings to which reference is made. The words "inwardly" and "outwardly" refer to directions toward and away from the parts referenced in the drawings. A reference to a list of items that are cited as "at least one of a, b, or c" (where a, b, and c represent the items being listed) means any single one of the items a, b, or c, or combinations thereof. The terminology includes the words specifically noted above, derivatives thereof and words of similar import.

Figure 2:
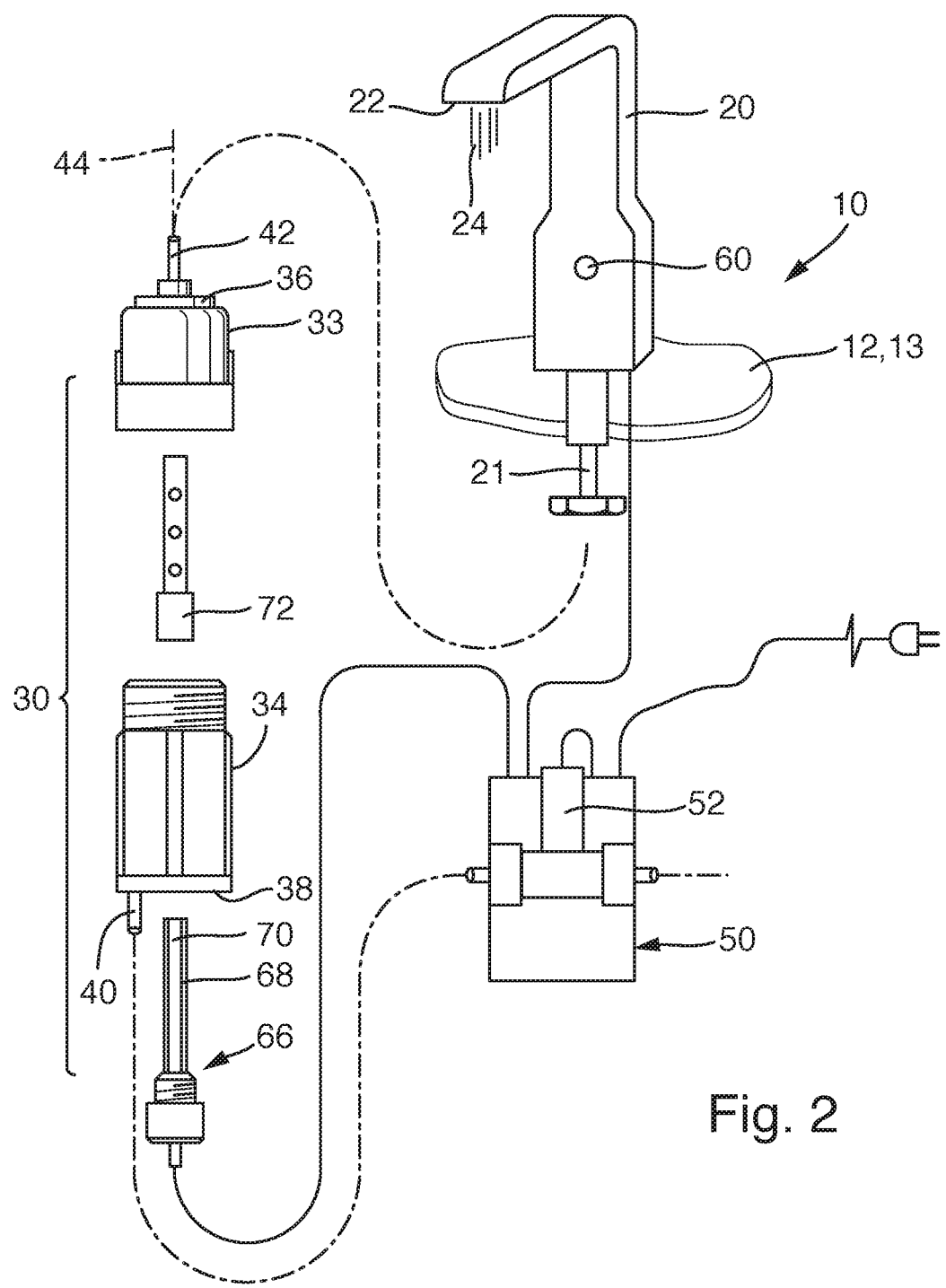
FIG. 2 is a schematic view of the components of the faucet assembly shown in FIG. 1.

Referring to FIGS. 1 and 2, a faucet assembly 10 is shown which includes an ozone generator 66. Ozone generators can infuse certain levels of ozone into the water being dispensed. As various bacteria are susceptible to ozone at various concentrations, with some being killed instantly and others requiring ozone levels greater than 2 ppm to be effective, faucet assemblies that generate ozone at the flow end are not always capable of generating this level of ozone in the water. The present faucet assembly addresses this by various means as described below to provide both a drain disinfection cycle as well as hand wash disinfecting mode.

As shown in FIGS. 1 and 2, the faucet assembly 10 includes a faucet armature 20 that is adapted to be connected to a sink 12 or a countertop 13, preferably such that the outlet 22 of the armature is adapted to discharge a flow of water 24 into the sink 12.

An ozone chamber 30 that is defined by housing 32 is provided as a separate unit that can be mounted below or adjacent to the sink 12. As shown in FIG. 2, the housing 32 is preferably formed with a top part 33 and a bottom part 34 that can be connected together in order to form the chamber 30. The housing 32 has a top 36 and a bottom 38, and the water inlet 40 and the water outlet 42 are connected to the chamber 30. Preferably, the water inlet 40 is located in the bottom 38 and the water outlet 42 is located in the top 36.

In one preferred arrangement, the ozone chamber 30 is cylindrical and is mountable with an axis 44, shown in FIG. 2, of the chamber 30 being vertical in the installed position. The chamber 30 preferably has a capacity of about 0.5 to 0.75 liters in one preferred embodiment. However, other capacities could be utilized, depending upon the particular application.

A flow control valve preferably in the form of a solenoid valve 52 is connected to the water inlet 40. A controller 50 is provided which preferably controls the solenoid of the flow control valve that acts as an actuator for opening and closing the valve body (not shown) located within the solenoid valve 52. An external pressurized water source is adapted to be connected to the solenoid valve 52.

A fluid conveying connection, such as a hose 56, is connected between water outlet 42 and the armature inlet 21 such that a water flow 24 can be delivered through the armature 20 through the armature outlet 22 and into the sink 12. The hose 56 can be a flexible hose made of polymeric material or can be formed of copper or another suitable metallic material.

As shown in FIGS. 1 and 2, a sensor 60 is provided that is adapted to detect a user's presence. The sensor 60 in a preferred embodiment is an IR sensor and is located on the faucet armature 20. However, other sensors could be used in connection with the faucet assembly 10 that detect a user's presence. For example, a sensor mat could be located in front of the sink 20 which is associated with the faucet assembly 10. As a further alternative, a break beam sensor could also be used.

As shown in detail in FIG. 2, an ozone generator 66 is located within the ozone chamber 30. In the preferred embodiment, the ozone generator 66 includes a threaded connection which is inserted into a threaded receiving opening in the bottom 38 of the housing 32 such that the cathode 68 and anode 70 of the ozone generator 66 extend within the ozone chamber 30. An outer cover 72 can be located over the cathode 68 and the anode 70, which can be more generally referred to in common as electrodes. Providing power to the ozone generator 66 generates a current through water located in the chamber 30 in order to create ozone and mixed oxidants as the current flows from the anode 70 to the cathode 68. One preferred ozone generator is available from Ozomax Inc. under the trade name "Ozopen". Details of the ozone generator and its function are also specifically explained in U.S. Pat. No. 8,440,080, which is incorporated herein by reference as if fully set forth. In the preferred arrangement, the ozone generator 66 extends up from the bottom 38 of the chamber 30 along the axis 44 of the chamber. Those skilled in the art will recognize that other ozone generators can be used.

Figure 3:
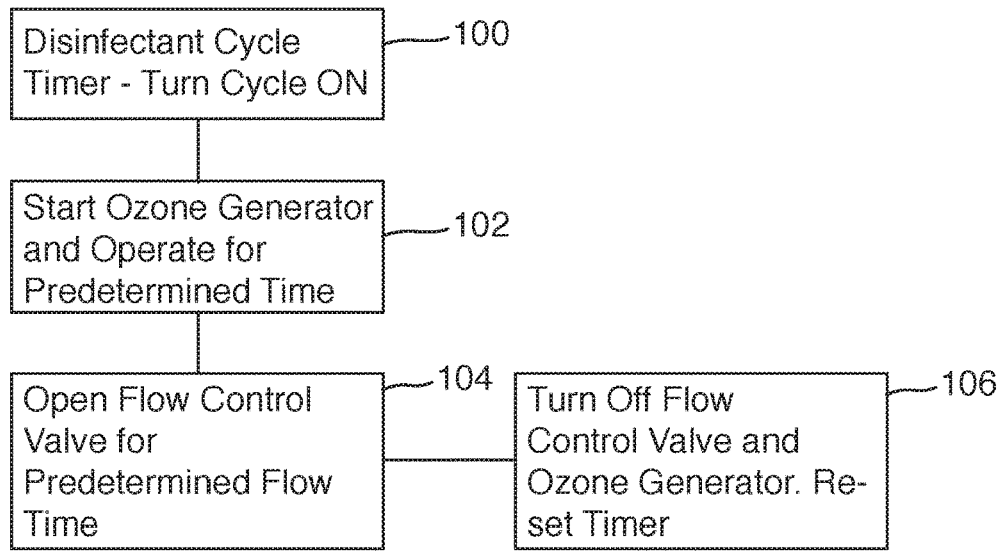
FIG. 3 is a flow chart showing a disinfectant cycle of the controller for the faucet assembly of FIG. 1.

The controller 50, which can be provided with the valve 52 or separately, depending on the specific application, is configured to receive signals from the sensor 60 and operate the solenoid valve 52 and the ozone generator 66. The controller 50 can be formed from a PLC or microprocessor with an associated memory, such as RAM or other solid state memory, that includes programming steps that are to be carried out by the controller 50. The controller 50 is preferably configured to run a cycle on an occasional basis in which the ozone generator 66 is activated, and after a predetermined time period, the controller 50 opens the solenoid valve 52 to flush a sink drain line 16 with ozone-rich water. This could be on a random basis or after a set time period, such as daily, every six hours, or other scheduled time intervals depending upon the particular application. Preferably, the ozone concentration in the water in the chamber 30 is raised to 0.6 ppm to 2 ppm in order to provide sufficient disinfecting ability via the ozone-rich water. One preferred cycle for the controller 50 shown in FIG. 3 which includes a disinfectant cycle timer built into the controller 50 which is turned to an "ON" status (as indicated at 100) on an occasional basis that can be preset in the factory or set by the user. Once the cycle is turned ON, the ozone generator 66 is started and operated for a predetermined time, as shown at 102. During this time the solenoid valve 52 remains off. The predetermined time in a preferred arrangement is approximately 20 seconds. This allows sufficient time for the ozone in the water to build up to between 0.6 and 2.0 ppm within the preferred volume of the ozone chamber, which in a preferred embodiment is 0.5-0.75 liters. Those skilled in the art will recognize both the time for the ozone generator 66 to run as well as the volume of the ozone chamber 30 can be changed, depending upon the particular application. Once sufficient ozone has built up such that the ozone concentration in the water is at the desired level, the solenoid valve 52 is opened for a predetermined flow time, as indicated in 104. The flow time is preferably based on the faucet flow rate and the volume of the ozone chamber 30 in order to allow a sufficient volume of the ozone-rich water to be discharged to flush the drain line 16 and preferably also a trap 18 located in the drain line, as shown in FIG. 1, to disinfect any materials in the sink drain. After the completion of the cycle, the controller 50 turns off the flow control valve 50, solenoid valve 52, and the ozone generator 66 and resets the timer, as indicated at 106.

In another aspect, the controller 50 can be further configured to activate the ozone generator 66 when the sensor 60 is activated by a user to wash a user's hands to open a solenoid valve 52. In this case, the sensor signals the controller 50 which then sends an open signal to the solenoid valve 52 as well as applies current to the ozone generator 66. When the sensor 60 no longer detects the user as being present, the sensor 60 signals the controller 50 which then turns off both the solenoid valve 52 and the ozone generator 66. Here, only a low concentration of ozone is added to the water flow which improves hand washing, but is insufficient to provide a full disinfecting function.

Figure 4:
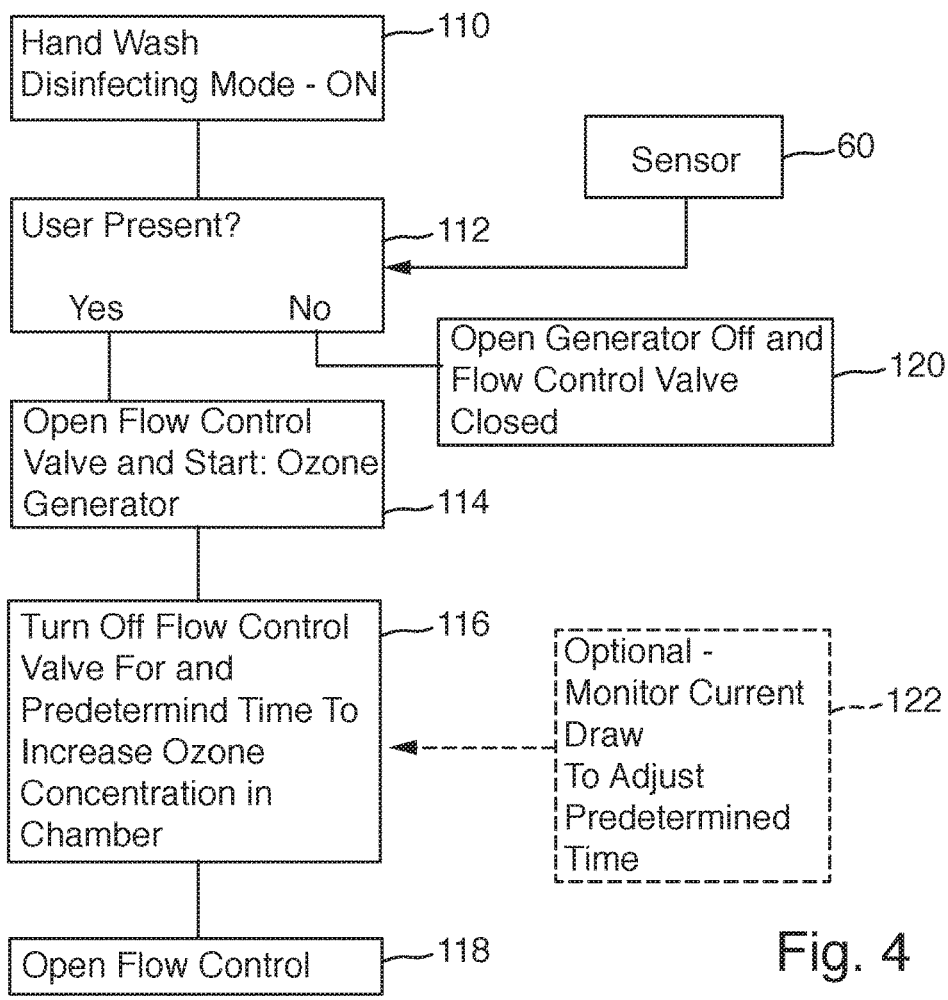
FIG. 4 is a flow chart showing a hand wash disinfecting mode of the controller.

In another aspect, the controller 50 is further configured to provide a disinfecting hand wash mode, which is shown in further detail in FIG. 4. Here, when the handwashing disinfecting mode is ON, as indicated at 110, the sensor 60 signals if a user is present, as indicated at 112. The controller 50 opens the solenoid valve 52 and starts the ozone generator 66, as shown at 114. When the user moves their hands away from the sensor 60 after initial delivery of water from the outlet 22 of the faucet armature 20, the controller 50 turns off the solenoid valve 52 while the ozone generator 66 continues to operate for a predetermined time to increase ozone concentration in the ozone chamber 30. Preferably, the ozone concentration in the chamber is increased to at least 0.2 ppm and preferably between 0.2 ppm and 0.6 ppm for disinfecting hand washing. The controller 50 then opens the solenoid valve 52 for rinsing with the ozone-rich water as indicated at 118.

One or more of these modes can be provided in the controller 50 of a given faucet assembly 10. For example, both the disinfecting hand washing mode and the disinfecting mode can be programmed into the same controller 50. In general, it is noted that in the disinfection cycle, the ozone generator is activated until the water in the ozone chamber has reached a second ozone concentration, and this second ozone concentration is higher than the first ozone concentration that is achieved for the disinfecting hand washing mode.

Still with reference to FIG. 4, optionally the controller 50 is configured to detect a current draw of the ozone generator 66 and adjust the pre-determined time period that the ozone generator 66 is activated while the solenoid valve 52 is off to control a concentration of ozone in the water in the ozone chamber 30. This is indicated at 122. In this case, the controller 50 calculates the amount of time that the ozone generator 66 must remain on dependent upon a current draw which is indicative of the Total Dissolved Solvents (TDS) in the water surrounding the ozone generator 66. The higher the TDS, the greater the conductivity of the water between the cathode 68 and the anode 70 which results in a higher ozone generation rate. Accordingly, the ozone generator 66 can be run for a shorter time by the controller 50 while still producing the desired concentration of ozone in the water in the chamber 30.

In a further improvement according to the invention, the controller 50 is configured to reverse a polarity of the cathode 68 and the anode 70 of the ozone generator 66 on an occasional basis. This helps to prevent the accumulation of minerals or other deposits on the cathode 68. The electrodes used for the cathode 68 and the anode 70 can be of the same material and accordingly, the reversal of the polarity reverses the positions of the cathode and anode.

According to the invention, the disinfectant cycle for the drain 16 and preferably a trap 18 associated therewith can reduce or eliminate the growing incident of hospital infections caused by sink drains. Additionally, as the faucet assembly 10 can be installed on existing sinks 12 or counters 13 adjacent to sinks, the opportunity for installing these in hospitals or other applications with space restrictions or where existing sinks that cannot be easily replaced can be accomplished in a simple and economic matter. Further, the faucet assembly 10 can also provide the same hands free faucet as previously known with the addition of the possibility of at least some ozone and mixed oxidant in the water being dispensed or a hand wash disinfecting mode which provides for greater disinfecting as discussed above.

While the preferred embodiment of the invention has been described in detail, those skilled in the art will recognize that other changes could be made to the faucet arrangement without departing from the scope of the present invention. Other arrangements could be provided and the specific configuration could be varied without departing from the scope of the present invention. Accordingly, the scope of the invention should not be limited by the preferred embodiments discussed above and instead should be defined by the claims as noted below.

What is claimed is:

1. A faucet assembly, comprising:
    an armature that is adapted to be connected to a sink or a counter top, the armature includes an outlet adapted to discharge a water flow into the sink;
    an ozone chamber defined by a housing having a top and a bottom, and a water inlet and a water outlet connected to the ozone chamber;
    a flow control valve connected to the water inlet;
    a fluid conveying connection between the water outlet and the armature;
    a sensor that is adapted to detect a user's presence;
    an ozone generator located within the ozone chamber; and
    a controller configured to receive signals from the sensor and operate the flow control valve and the ozone generator, the controller being configured to run a disinfection cycle at least on an occasional basis in which the ozone generator is activated, and after a pre-determined time period, the controller opens the flow control valve to flush a sink drain line with ozone-rich water.

2. The faucet assembly of claim 1, wherein the ozone-rich water is adapted to disinfect water located in a trap of the sink drain line.

3. The faucet assembly of claim 1, wherein the controller is further configured to activate the ozone generator when the sensor is activated by a user to wash a user's hands and to open the flow control valve.

4. The faucet assembly of claim 3, wherein the controller is further configured to provide a disinfecting hand wash mode in which, when the sensor no longer detects a user's hands due to moving away from the sensor after an initial delivery of water, the controller is adapted to turn off the flow control valve for a predetermined time period and continues to allow the ozone generator to operate such that an ozone concentration in the water within the chamber is adapted to increase to at least 0.2 ppm, and then is adapted to turn on the control valve.

5. The faucet assembly of claim 1, wherein the chamber is cylindrical and is mountable with an axis of the chamber being vertical.

6. The faucet assembly of claim 5, wherein the chamber has a capacity of about 0.5 liters to 0.75 liters.

7. The faucet assembly of claim 5, wherein the ozone generator extends along the axis of the chamber.

8. The faucet assembly of claim 1, wherein the sensor is an IR sensor and is located on the armature.

9. The faucet assembly of claim 1, wherein the controller is further configured to detect a current draw of the ozone generator and adjust the pre-determined time period that the ozone generator is activated to control a concentration of ozone in the water in the chamber.

10. The faucet assembly of claim 1, wherein the controller is configured to reverse a polarity of a cathode and an anode of the ozone generator on an occasional basis.

11. The faucet assembly of claim 1, wherein the controller is further configured to activate in a hand wash mode, in which the sensor detects a user and opens the flow control valve and, when a user moves their hands away from the sensor after an initial delivery of water, the controller is adapted to turn off the flow control valve for a predetermined time period and continues to allow the ozone generator to operate such that a first ozone concentration is reached in the water within the chamber, and then is adapted to turn on the control valve, and in the disinfection cycle, the ozone generator is activated until the water in the ozone chamber has reached a second ozone concentration, wherein the second ozone concentration is higher than the first ozone concentration.

12. The faucet assembly of claim 5, wherein the ozone generator extends up from the bottom of the housing into the chamber.

13. A method of disinfecting a sink trap, comprising:
providing an armature that is adapted to be connected to a sink or a counter top, with the armature including an outlet, an ozone chamber defined by a housing having a top and a bottom, and a water inlet and a water outlet connected to the ozone chamber, a flow control valve connected to the water inlet, a fluid conveying connection between the water outlet and the armature, a sensor that is adapted to detect a user's presence, an ozone generator located within the ozone chamber, and a controller configured to receive signals from the sensor and operate the flow control valve and the ozone generator;
running a disinfection cycle by the controller activating the ozone generator, and
after a pre-determined time period, the controller opening the flow control valve to flush a sink drain line with ozone-rich water.

14. The method of claim 13, wherein the controller opens the flow control valve for a predetermined flow time.

15. A method of providing a disinfecting hand wash, comprising:
detecting when a user is present at a sink by a sensor;
a controller receiving a signal when a user is present and opening a flow control valve for water and starting an ozone generator located in a chamber that receives the water from the flow control valve, and discharges the water into the sink;
the controller turning off the flow control valve for a predetermined time to increase an ozone concentration in the water in the chamber; and
the controller opening the flow control valve to discharge the water with the increased ozone concentration from the chamber into the sink.

16. The method of claim 15, further comprising monitoring a current draw of the ozone generator and adjusting the predetermined time based on the current draw.

17. The method of claim 15, further comprising:
turning off the ozone generator and closing the flow control valve.

18. The method of claim 15, further comprising:
turning on a disinfectant cycle based on a timer;
starting the ozone generator and operating the ozone generator for a predetermined time for the disinfecting cycle and increasing an ozone concentration of the water in the chamber;
opening the flow control valve for a predetermined flow time and discharging the water with the increased ozone concentration from the chamber into the sink; and
turning off the flow control and the ozone generator.

19. The method of claim 18, further comprising:
resetting the timer.

* * * * *